United States Patent [19]
Lohnes et al.

[11] Patent Number: 5,482,626
[45] Date of Patent: Jan. 9, 1996

[54] ANALYTICAL LIQUID TEST SAMPLE FILTRATION APPARATUS

[75] Inventors: Brent C. Lohnes, Soda Springs; Terry D. Turner; Kerry M. Klingler, both of Idaho Falls; Michael L. Clark, Menan, all of Id.

[73] Assignee: Lockheed Idaho Technologies Company, Idaho Falls, Id.

[21] Appl. No.: 171,132

[22] Filed: Dec. 20, 1993

[51] Int. Cl.$^6$ .................................................... G01N 35/02
[52] U.S. Cl. .................... 210/340; 210/325; 210/328; 210/329; 210/361; 422/101
[58] Field of Search ...................................... 210/361, 781, 210/782, 323.1, 324, 325, 340, 328, 329; 422/72, 101

[56] References Cited

PUBLICATIONS

BenchMate Workstations, "IMAGINE: HPLC Without Manual Sample Preparation" brochure, Zymark, 1990.
"Environmental Lab Automation", Zymark brochure, 1991.
BenchMate Workstations, "Personal Automation for Sample Preparation and Auto–Sampling" brochure, Zymark, 1991.

*Primary Examiner*—Robert A. Dawson
*Assistant Examiner*—David Reifsnyder
*Attorney, Agent, or Firm*—Wells St. John Roberts Gregory & Matkin

[57] ABSTRACT

A liquid sample filtration apparatus includes: a) a module retaining filter elements; b) a filter clamping and fluid injection apparatus positioned relative to the module to engage a filter element thereon, and includes a pair of first and second opposing engageable members to sealing engage a filter element therebetween; c) an inlet tube connected to an opposing engageable member; d) an outlet tube connected to an opposing engageable member; e) a motor to move the module relative to the filter clamping and injection apparatus to register filter elements on the module to the clamping and injection apparatus; and f) a motor associated with the filter clamping and injection apparatus to move the opposing engageable members into substantial sealing fluid communication relative to a filter element on the module. An apparatus for engaging opposing ends of a filter element includes: a) a member having a recess configured to engage one end of a filter element, including a first fluid passage communicating with the recess to pass fluid between the recess and externally of the member; and b) a second member positioned in opposing juxtaposition relative to the other member, and having a projection sized and shaped to matingly fit within the other member recess, the second member projection including a second recess configured to engage the other end of the filter element, the second member including a second fluid passage communicating with the second recess to pass fluid between the second recess and externally of the second member.

29 Claims, 5 Drawing Sheets

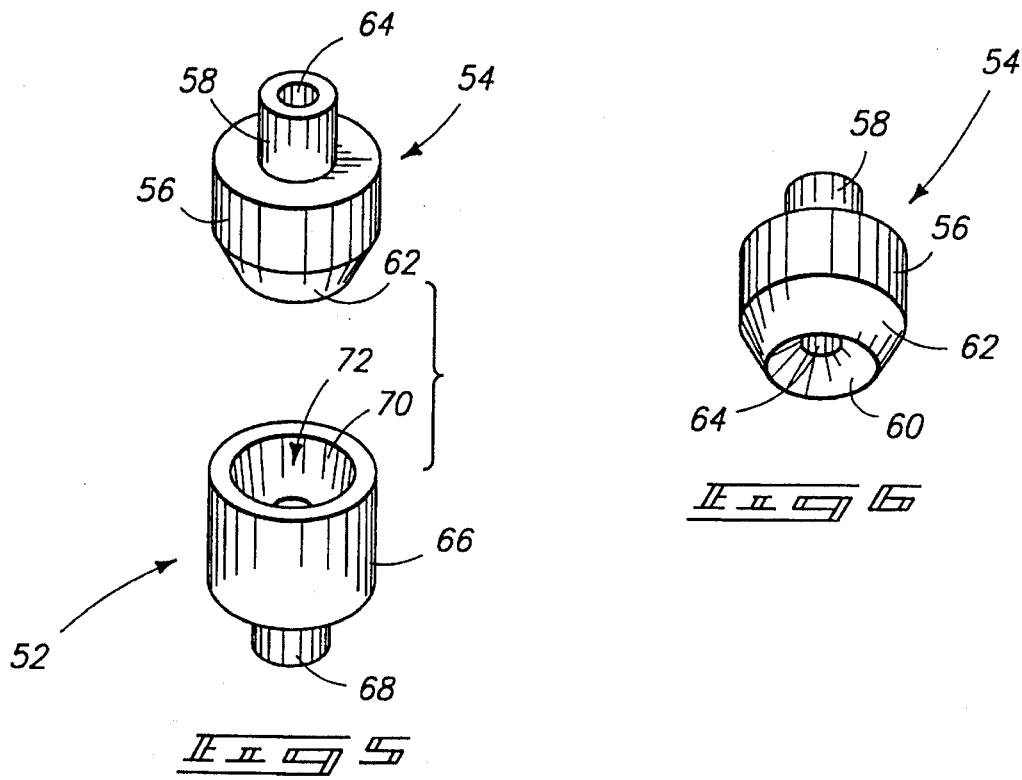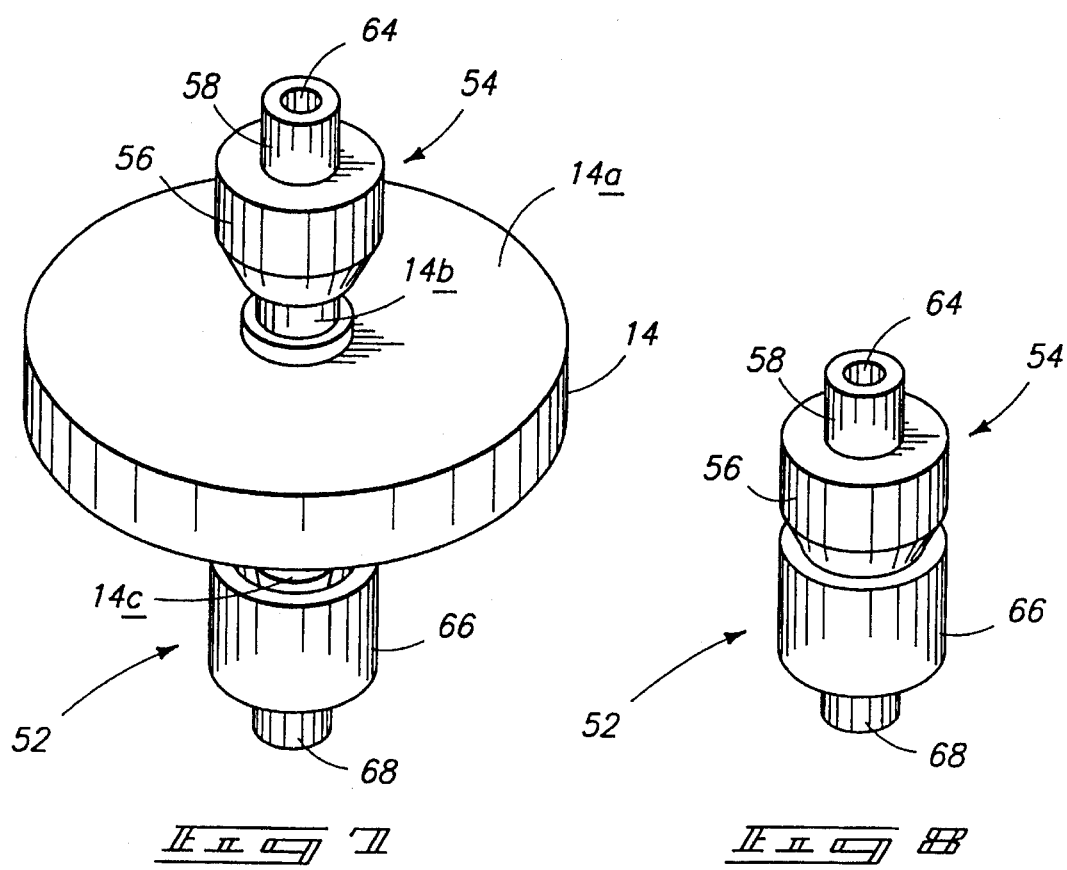

ANALYTICAL LIQUID TEST SAMPLE FILTRATION APPARATUS

CONTRACTUAL ORIGIN OF THE INVENTION

The United States Government has rights in this invention pursuant to Contract No. DE-AC07-76ID01570 between the U.S. Department of Energy and EG&G Idaho, Inc.

TECHNICAL FIELD

This invention relates to liquid test sample filtration apparatus and methods.

BACKGROUND OF THE INVENTION

Environmental chemistry includes the analysis of soil samples to qualitatively and quantitatively determine presence of contaminants. Current analytical chemistry procedures are very time consuming and labor intensive, and will not realistically meet future needs generated by the U.S. Department Of Energy's environmental restoration and waste management programs.

Accurate soil sample analysis is a critical determination. Before remediation of problem areas can begin, the type and extent of contamination must be determined. Samples to be analyzed must be retrieved from the site and transported to a facility capable of analytical chemistry. The soil sample is processed to remove constituents that are not of interest and to isolate the contaminating substances. Once the sample has been processed and prepared, it is submitted for spectral analysis to determine content and concentration. Now, a trained scientist is required to determine if the concentration levels indicate contamination or are just indicative of background levels. As a precaution, spiked samples are processed with the actual sample. These spiked samples are used to verify that the process is yielding direct results and all must be analyzed the same way.

The protocol that includes all of the tasks from sample retrieval to output of characterization information has been designated as a standard analysis method, or SAM for short. If SAMs could be automated, laboratory technicians would be able to perform analytical analysis in a fraction of the time and cost of conventional prior art methods.

A SAM typically consists of three categories of operations: sample preparation, analysis, and data interpretation. Imbedded within the different areas of the SAM are many smaller tasks, such as weighing the sample or concentrate. Often these steps are repeated several times during the course of a SAM and are common to several SAMs. In accordance with an aspect of the invention, the equipment required to perform individual steps has been developed into automated modules.

Common to many SAMs are filtration and liquid concentration. This invention principally concerns methods and apparatus for filtering previously concentrated liquid samples. As a result of the typical concentration procedures, suspended solids precipitate out of the sample solution. To avoid equipment damage, these solids are filtered out of the sample. In the current procedure, a syringe is used to draw approximately 10 milliliters of sample through a filter. If the solids content is high, the filter holder must be disassembled to replace the paper filter and reassembled. Sometimes this must be performed three to four times per sample. It would be desirable to improve upon prior art techniques in liquid sample filtration.

Although this invention spawned from research associated with development of a standard laboratory module in conducting an overall automated process for analyzing test samples in accordance with EPA standards, those skilled in the art will find other uses of the invention which is intended to be limited only by the accompanying claims appropriated interpreted in accordance with the Doctrine of Equivalents.

BRIEF DESCRIPTION OF THE DRAWINGS

Preferred embodiments of the invention are described below with reference to the following accompanying drawings.

FIG. 5 is an enlarged diagrammatic perspective view of opposing engageable members of the FIG. 4 apparatus.

FIG. 6 is an upward viewing perspective view of one of the FIG. 5 engageable members.

FIG. 7 is a perspective view of the FIG. 5 engageable members shown engaging a filter element therebetween.

FIG. 8 is a perspective view of the FIG. 5 engageable members shown engaging one another.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In accordance with an aspect of the invention, a liquid test sample filtration apparatus comprises:

a module configured to hold a plurality of filter elements in spaced relation;

a filter clamping and fluid injection apparatus positioned relative to the module to engage a filter element thereon;

cycling means for moving the filter clamping and fluid injection apparatus and module relative to one another for registering filter elements on the module to the filter clamping and fluid injection apparatus;

clamping means for moving the filter clamping and fluid injection apparatus into substantial sealing fluid communication relative to a filter element on the module; and means for passing fluid through the filter clamping and fluid injection apparatus and a filter clamped relative to the filter injection apparatus.

In accordance with another aspect of the invention, a rotatable module for a liquid test sample filtration apparatus comprises:

a round carousel body having opposing faces and a peripheral edge;

a series of filter element retainers provided about the carousel at the peripheral body edge, the filter element retainers being configured to retain a series of filter elements on the carousel for engagement by the filter clamping and fluid injection apparatus; and a cut-out slot provided in the carousel peripheral edge between two of the filter element retainers, the cut-out slot extending from one opposing face to the other and being sufficiently large to enable clamping engagement of the first and second opposing members therethrough.

In accordance with a further aspect of the invention, an apparatus for engaging opposing ends of a filter element comprises:

a first member having a first recess configured to engage one end of a filter element, the first member including a first fluid passage communicating with the first recess to pass fluid between the first recess and externally of the first member; and a second member positioned in opposing juxtaposition relative to the first member, the second member having a projection sized and shaped to matingly fit within the first member recess, the second member projection including a second recess configured to engage the other end of the filter element, the second member including a second fluid passage communicating with the second recess to pass fluid between the second recess and externally of the second member.

Figure 1:
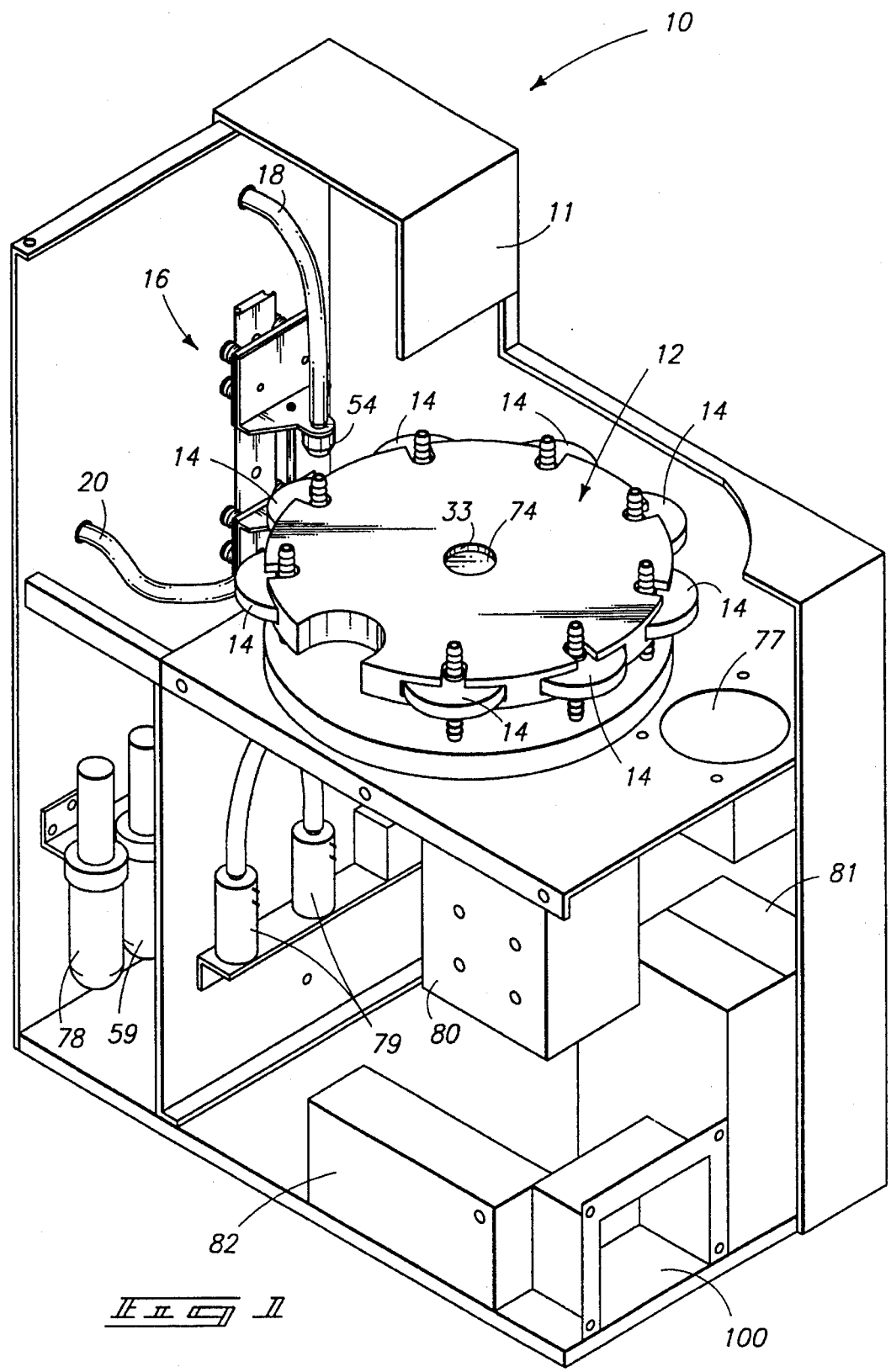
FIG. 1 is a cut-a-way diagrammatic view of a liquid sample filtration apparatus in accordance with the invention.

More specifically and with reference to the Figures, and first with reference to FIG. 1, there illustrated is a liquid test sample filtration apparatus indicated generally and diagrammatically with reference numeral 10. Such includes an aluminum support frame 11. This principally houses a module 12 which retains a plurality of filter elements 14 in spaced relation in the peripheral region of module 12. Module 12 is configured and mounted for rotation. A filter clamping and fluid injection apparatus 16 is positioned relative to module 12 to separately engage the filter elements positioned thereon. Fluid would flow into the apparatus via tubing 18, through a selected filter 14, with filtered fluid passing from the apparatus via associated tubing 20. Alternately, tubing (not shown) could be provided to feed filtered fluid to receptacle 100 for filling an outlet vial (not shown). Various associated pneumatics and computer hardware are provided in the base of apparatus 10, and will be described subsequently.

Module 12 is preferably designed to be reusable with the individual filter elements being discarded and replaced after a single use. A discrete liquid sample volume would be filtered by passing through a single filter 14. A cleaning operation of filter clamping and fluid injection apparatus 16 would then occur, followed by positioning of another filter element 14 relative to apparatus 16 for filtering of another discrete sample volume.

Figure 2:
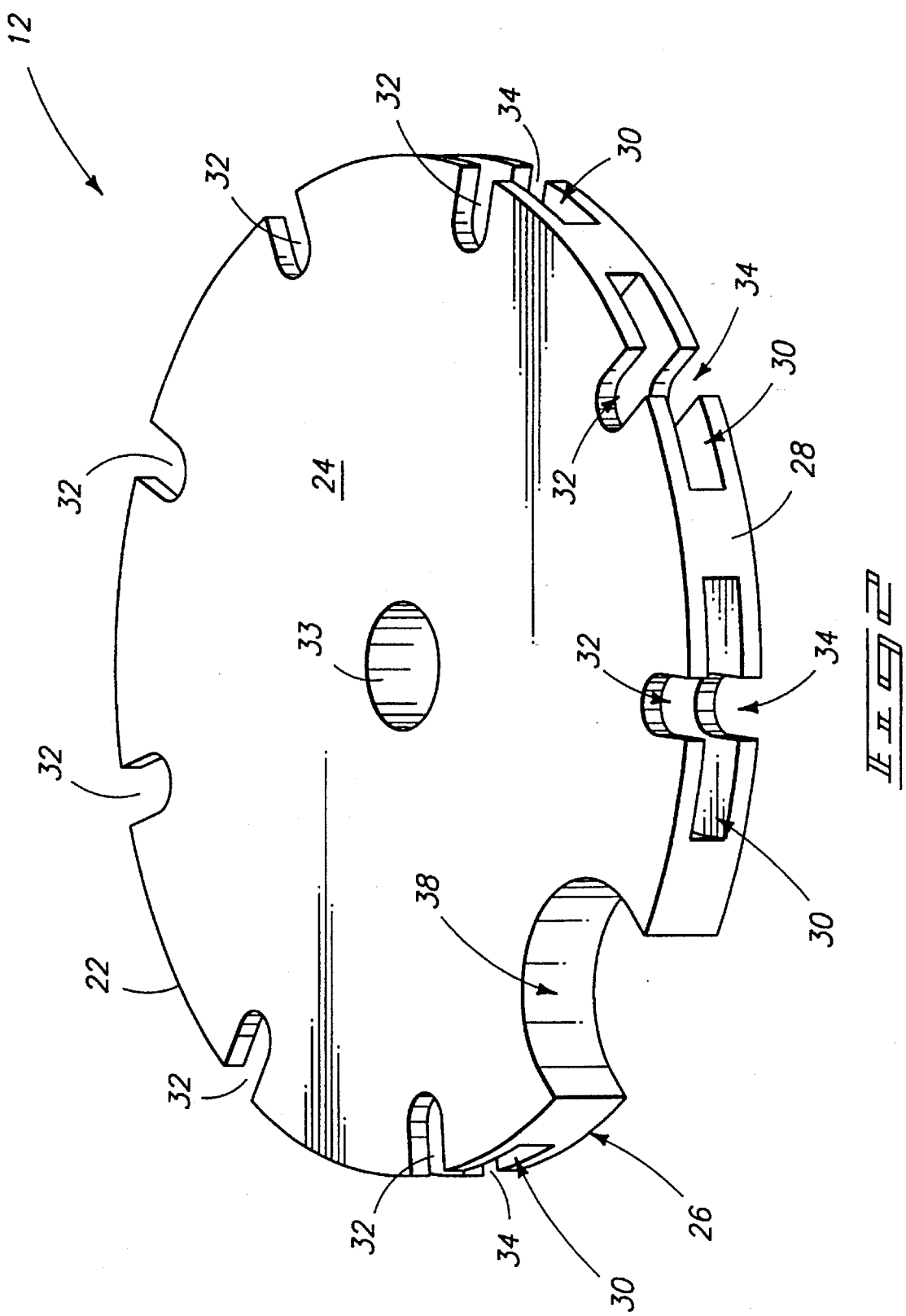
FIG. 2 is an enlarged perspective view of a filter module utilized in the FIG. 1 apparatus.
Figure 3:
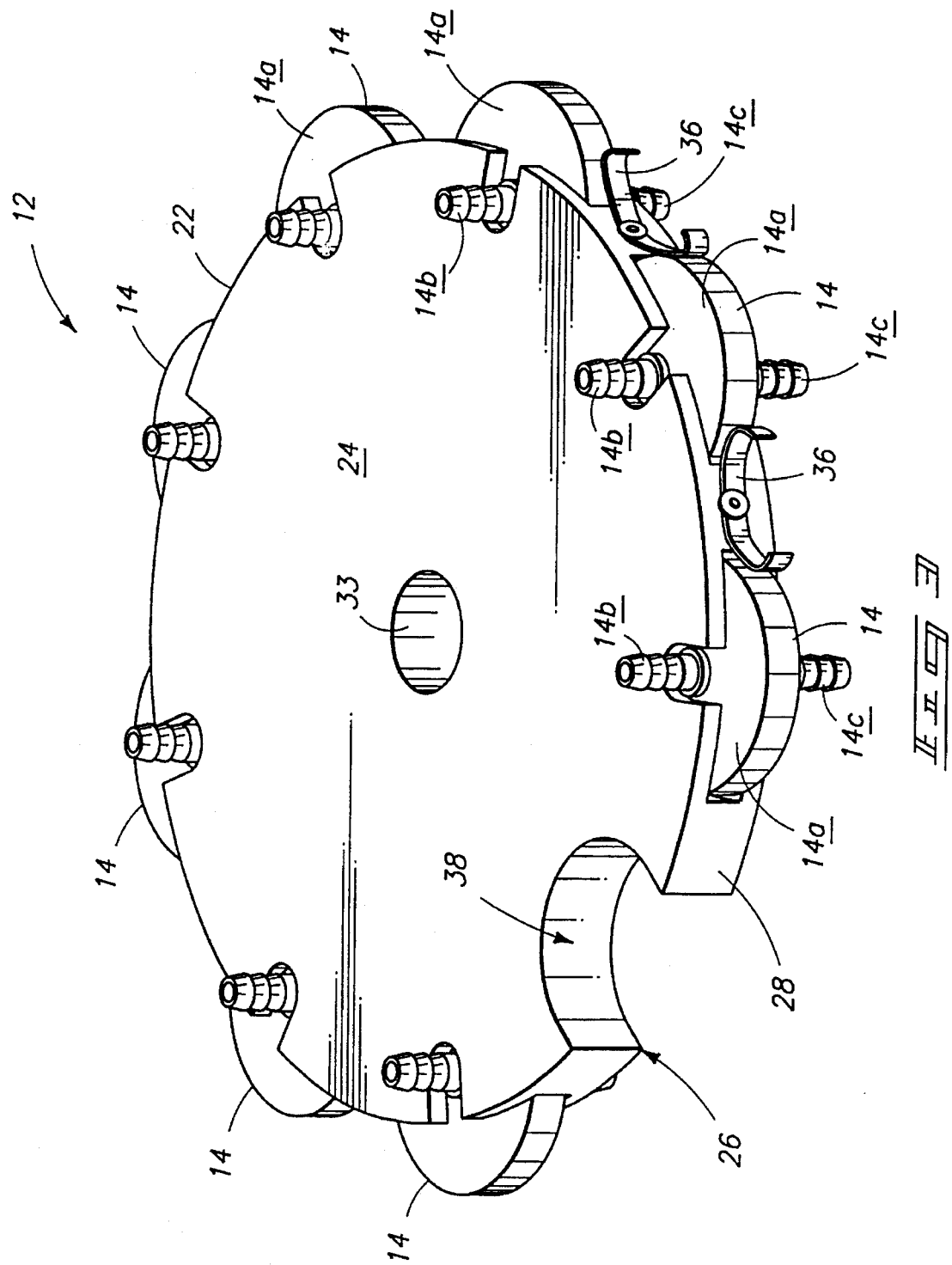
FIG. 3 is a view of the FIG. 2 module retaining a series of filter elements.

Reference is made to FIGS. 2 and 3 for a description of module 12. Such comprises a circular, disk-like, round carousel body 22 having opposing faces 24, 26 and a peripheral edge or region 28. An example material for body 22 is Delrin™ polymer. A series of eight semi-cylindrical slots or recesses 30 are provided into and about peripheral edge region 28. Such are sized to retain the main body portion 14a (FIG. 3) of the illustrated top-like or saucer-like filters with which the preferred embodiment apparatus is intended to be used. Example filters are Whatman Polydisc TF 50 millimeter filters made by Whatman, of Clifton, N.J. Alternate shaped filters and carousel bodies 22 could also of course be used without departing from the principals and scope of the invention.

A pair of additional smaller semi-cylindrical slots or recesses 32 and 34 are also centrally provided with respect to each semi-cylindrical slot 30. Slot 32 extends from upper face 24 through carousel body 22 downwardly to large semi-cylindrical slot 30. Semi-cylindrical slot 34 in similar fashion extends through carousel body 22 from lower face 26 to larger semi-cylindrical slot 30. Slots 32 and 34 are aligned and adapted to receive the opposing stems 14b and 14c respectively (FIG. 3), which extend outwardly from the central disk-like portions 14a of filter elements 14.

A series of clips 36 (FIG. 3) are riveted, bolted or otherwise fastened to body 22 peripheral edge region 28 between adjacent semi-cylindrical slots 30. Such clips 36 are only shown in FIG. 3 for clarity, and even then only two such clips being shown. Clips 36 would be comprised of a stainless steel metal which outwardly flares in a springed manner to tightly, yet removably, retain a filter element within slots 30, 32 and 34.

Slots 30, 32, 34 and clips 36 in cooperation constitute a series of filter element retainers which are provided about the carousel at its peripheral body edge for retaining a series of filter elements. Such are retained for engagement by filter clamping and fluid injection apparatus 16 (FIG. 1), as will be apparent from the continuing discussion.

Carousel body 24 further includes a cut-out slot 38 provided into peripheral edge region 28 between two filter element semi-cylindrical slots 30. Cut-out slot 38 extends from upper face 24 to lower face 26 and is sufficiently large to enable clamping engagement of components of filter clamping and fluid injection apparatus 16 therethrough, as also will be apparent from the continuing discussion. A central hole 33 is provided from body face 24 to body face 26 to receive a drive shaft 74 (FIG. 1) to rotatably drive carousel module 12 relative to filter clamping and fluid injection apparatus 16.

Carousel module 12 is designed to be removable from apparatus 10 to discard used filter elements 14, and enable another series of filter elements 14 to be readily positioned for use. Further, the modular carousel design allows other configurations to be utilized and mounted for alternative filtration purposes. Each carousel wheel will be specifically designed and fabricated for use with a given type of filter.

Figure 4:
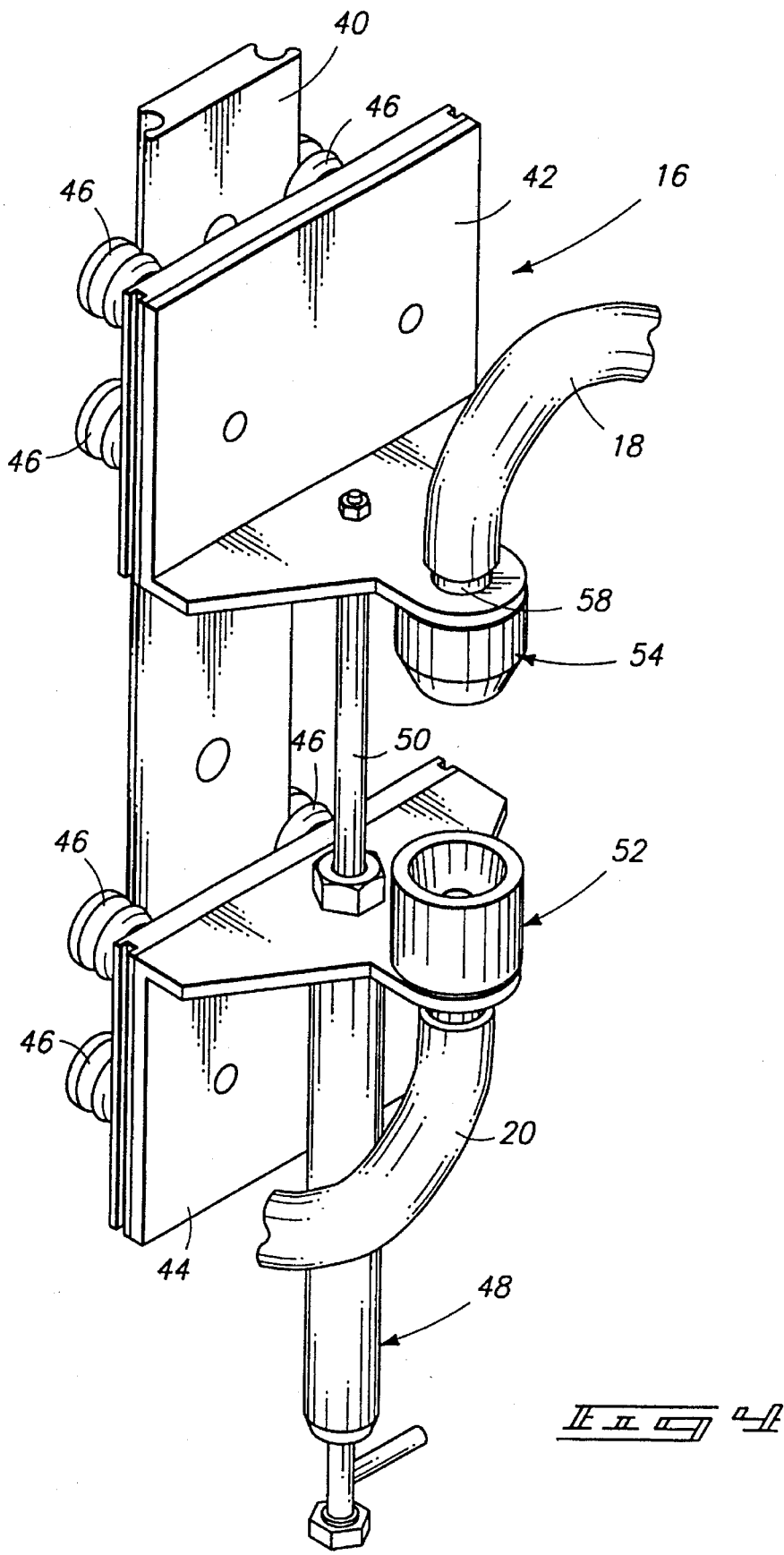
FIG. 4 is an enlarged perspective view of a filter clamping and fluid engaging apparatus utilized in the FIG. 1 apparatus.

Aspects of the filter clamping and fluid injection apparatus 16 are now described with reference to FIGS. 4–8. Referring first to FIG. 4, apparatus 16 is comprised of a support bar or rail 40 and opposing frame members or brackets 42 and 44 which are movable relative thereto. A series of four rollers 46 mount rearwardly to each of frame members 42 and 44 to movably and slidably support such frame members relative to rail 40. Members 42 and 44 are moved relative to one another via a pneumatic cylinder assembly 48, which would include a piston rod 50. Stops (not shown) can be provided to limit upward and lower travel of frame members 42 and 44. All materials of construction should of course be chemically resistant.

Now referring collectively to FIGS. 4–8, mounted to opposing frame members 42 and 44 are a pair of opposing first and second opposing engageable members 54, 52, respectively. Members 52 and 54 are adapted to sealingly engage relative to a filter element 14 on module 12, and also to sealingly engage relative to one another.

More specifically, first and second members 54 and 52 are mounted to brackets 42 and 44 respectively to be positioned in opposing juxtaposition relative to one another. Pneumatic cylinder 48 constitutes a motor to move members 54 and 52 into substantial sealing fluid communication relative to a filter element on module 12 and relative to one another. First member 54 is comprised of a body 56 which defines an upper extending male connection 58 for connection with sample inlet supply tube 18 (FIG. 4). Body 56 (FIG. 5)

further includes a downwardly formed male projection 62 which is conical in shape. A lower conical recess 60 is formed within projection 62 to engage as upper stem 14b of a filter element 14 (FIGS. 6 and 7). A fluid passage 64 communicates with recess 60 to pass fluid between recess 60 outwardly of projection 58 and externally of first member 54.

Second member 52 is comprised of a central body 66 and downward male projection 68 for connection with a sample outlet tube 20 (FIG. 4). Body 66 is further provided with a conical recess 70 configured to engage a bottom stem 14c of a filter element 14 (FIGS. 5 and 7). Body 66 further includes a fluid passage 72 extending outwardly through projection 68 and to recess 70 to pass fluid between first recess 70 and externally of first member 52. Conical projection 62 of first member 54 is sized and shaped to matingly fit within first member recess 70 to create a fluid tight seal between first member 54 and second member 52 even when a filter element 14 is not positioned therebetween (FIG. 8).

Referring again to FIG. 1, carousel module 12 is mounted for rotation about a centrally extending shaft 74. A suitable stepper motor (not shown) rotatably drives and indexes or registers modular carousel 12 for positioning any one of filter elements 14 or slot cut-out 38 relative to member 54 and to member 52 (hidden in FIG. 1). Such stepper motor in part comprises a cycling means for moving filter clamping and fluid injection apparatus 16 and module 12 relative to one another for registering individual filter elements on the module to the filter clamping and fluid injection apparatus. Alternate means and configurations could of course be provided to enable movement of one of a series of modularly retained filter elements relative to a filter clamping and fluid injection apparatus.

As will be appreciated by the artisan, various appropriate hardware can be configured within housing 10 for providing the desired functions, with only examples being diagrammatically represented in FIG. 1 and described below. For example, a cooling fan 77 can be provided for cooling the apparatus. Various electronic subassemblies and valving may also be utilized, such as a regulator 78 and a pneumatic filter 59, pneumatic valves and tubing 79, a power supply housing 80, computer housing 81, and stepper motor controller housing 82.

These and other various components will of course be designed and appropriately sized by the artisan depending upon determined needs and capacities. For example in our specific design, frame 11 was constructed of T1100 aluminum bent into the desired illustrated configurations. Flush mount captivated screws and Pem nuts (Penn Engineering and Manufacturing Corp. of Danboro, Pa.) were used to improve ease of assembly and maintenance. Cooling fan 77 was selected to dissipate approximately 200 Watts during a worst case scenario, and was selected to be a 27 CFM brushless DC cabinet fan. In addition to cooling effects in the above preferred design, the fan also creates a purged and pressurized enclosure, reducing the hazardous location classification from Class I, Division 2 to nonhazardous pursuant to NFPA 496, Chapter 2 standards. Elevated fan placement was selected due to anticipation that all solvents utilized in the process being heavier than air.

The step motor utilized was produced by American Precision Industries of Buffalo, N.Y. and was a Hybrid NEMA Size 23. Because the motor is a Hybrid, it is capable of being used in full step, half step or microstep applications. An Absocoder™ (available from Enprotech Corp. of Livonia, Mich.) is mounted to the NEMA Size 23 Step Motor. Such is an absolute encoder that used magnetic fields to determine position.

Rail or slideway 40 was made by HEPCO of Pittsburg, Calif., and was a Generation II, Small Slideway Section NS-25. Frame members 42 and 44 were made of metal. Pneumatic cylinder 48 was made by American Cylinder Co., Inc. of Peotone, Ill. A Hall Effect Switch, Stainless Steel Body Air Cylinder with a four inch stroke, equipped with Viton seals, bumpers and right angle flow control valves, was chosen for its chemical resistance, smoothness of operation, adjustability gained by the flow control valves and controllability provided by the Hall Effect Switch. The cylinder was a double acting nose mount providing a controlled stroke for both closing and opening the clamp.

Pneumatic valves were 24 VDC, Clippard ETO-3, Minirnatic Electronic/Pneumatic Interface Valves available from Clippard Instrument Laboratory of Cincinnati, Ohio. One normally open, 3-way poppet valve and one normally closed, 3-way poppet valve were chosen for controlling the pneumatic cylinder. By offsetting the valves, normally open/normally closed, apparatus 16 can be set to close in the event of a power failure.

Fluid routing valves were selected to be solenoid operated Teflon™ isolation valves made by BIO-CHEM Valve Corporation of Boonton, N.J. Such valves were chosen for their low power consumption, isolated solenoid, low dead volume and all Teflon™ wetted parts. Operating pressure was under vacuum to 20 psi pressure. A two-way valve is used as a backflow preventer, and a three-way valve is used to route the sample extract to either waste or a sample outlet port. Tubing utilized to carry the fluids was FEP Teflon™. Such was transparent having a ⅛ inch outside diameter and a ¹⁄₁₆ inch inside diameter. The length is field-fit to achieve the shortest distance between end points and not the tubing.

Fluid handling fittings were selected to be of two types, the first being an Upchurch (Oak Harbor, Wash.) and the second being Furon (Anaheim, Calif.). The selected Upchurch fitting was a ¼–28 screw-in design with a flat bottom ferrule. Such were utilized to connect the tubing to the valves. Upchurch fittings provide a zero dead volume between the fitting and the valve body. Several different styles of Furon fittings were used in the module.

A standard STD bus computer and associated input/output cards were selected. An STD bus computer system was selected for its small size and ability to be programmed through a personal computer. Such provides flexibility to include all computing power inside the module case.

A Ziatech ZT 8801 (San Luis Obispol, Calif.) single board V40, STD bus computer is used for the processing power. The V40 processor is code-compatible with the Intel 8088 CPU, and features an interrupt controller, three counter timers, and a serial channel integrated with the core processor. The serial channel on the ZT 8801 is configured to RS-232 standards, and is complimented on-board by up to 48 points of digital I/O, and SBX expansion module connector, and 512 Kbytes EPROM/flash, and 1 Mbyte of RAM. The ZT 8801 is supported by Ziatech's STD DOS and STD ROM software environments. Common I/O software support is provided by Ziatech's STD device driver package. A general purpose interface bus (GPIB) expansion module is attached to the SBX connector on the ZT 8801 computer card.

There is a standard (STD) bus computer which interfaces through a GPIB communications port with an external transfer module for moving fluid to and from apparatus IO. The STD board plugs into a Versalogic VX32-04T (Eugene, Oreg.), 4 slot STD 32 bus industrial card cage. The STD 32 bus accommodates an 8 to 32 bit data path with dynamic bus sizing and can drive up to 32 address lines. Expanded interrupt and DMA modes are also supported. Slot specific signals for a true multiprocessing system with arbitration was provided. The STD 32 card edge connectors and bus are compatible with existing STD 80 cards as well as 114 and 136 finger STD 32 cards.

The back plane used in V32 Series card cages features a 0.093 inch multilayer circuit board which provides controlled impedance, reduced capacitance signal lines for dependable, high speed operation. A multilayer design provides very low impedance paths for supply voltages for negligible supply noise or voltage drop at each card slot.

The STD bus card cage is powered by a Versalogic VL-PS50 power supply. Such is a compact, high efficiency power supply designed specifically for the V32 Series STD bus card cages.

The stepper motor controller used was an Inland Motor SMC-500 (Inland Motor of Radford, Va.) advanced programmable motion controller. Such is a hybrid programmable motion controller with a built-in bipolar chopper driver, onboard nonvolatile RAM, and programmable inputs and outputs, and a RS-232C serial interface. Such controller utilizes a single unregulated power supply for all internal voltages, including signal-level voltages.

The RS-232C compatible serial I/O port (DB-9f) allows command buffer and status to be exchanged at standard baud rates from 75 to 9600. Baud rates are set by the user with a DIP switch. Communications are 8 bit, 1 stop bit, no parity.

Two types of sensors were utilized in the filtration module, namely a sonic bubble detector (Introtek International of Edgewood, N.Y.) and photoelectric switches. Specifically, two Micro-Switch (FE5F) double fiber optic photoelectric controllers were utilized. Such are available from Micro Switch of Freeport, Ill. Three diffuse scan fiber optic cables were utilized to detect filter presence, carousel presence, and output vial presence in receptacle 100 and one through scan fiber optic cable to prevent the output vial from overfilling. Signals generated from the optic sensors are sent to the computer which takes the required action or produces an error message.

Bubble sensors utilized were Introtek 900-SC24-125 transducers with E10-3000-125 electronics, available from Introtek International of Edgewood, N.Y. Such utilizes 115VAC and uses a relay output. The ⅛ inch Teflon™ tubing leaving the pump passes through the transducer, which uses ultrasonics to monitor flow through the tubing. When a bubble passes through the sensor, a signal is generated to close the relay.

The above described filtration apparatus spawned out of research directed toward development of an automated module for an integral analytical system for soil samples. Its primary purpose was directed to remove particulate of 0.5 micron and larger from semi-volatile organic soil extracts prior to their injection into a Gel Permeation Chromatography Column.

In compliance with the statute, the invention has been described in language more or less specific as to structural, compositional and methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A liquid test sample filtration apparatus comprising:

a module configured to hold a plurality of filter elements in spaced relation;

a filter clamping and fluid injection apparatus positioned relative to the module to engage a filter element thereon, the filter clamping and fluid injection apparatus including a pair of first and second opposing engageable members to sealing engage a filter element on the module therebetween;

cycling means for moving the filter clamping and fluid injection apparatus and module relative to one another for registering filter elements on the module to the filter clamping and fluid injection apparatus;

clamping means for moving the filter clamping and fluid injection apparatus into substantial sealing fluid communication relative to a filter element on the module; and means for passing fluid through the filter clamping and fluid injection apparatus and a filter clamped relative to the filter injection apparatus.

2. The liquid test sample filtration apparatus of claim 1 wherein the module is configured and mounted for rotation.

3. The liquid test sample filtration apparatus of claim 1 wherein the module is configured and mounted for rotation, the module including a peripheral region, the peripheral region retaining the respective filter elements.

4. The liquid test sample filtration apparatus of claim 1 wherein the module is in the shape of a round carousel having a peripheral region, the respective filter elements being retained in the peripheral region.

5. The liquid test sample filtration apparatus of claim 1 wherein the cycling means is configured to move the module.

6. A liquid test sample filtration apparatus comprising:

a module configured to hold a plurality of filter elements in spaced relation;

a filter clamping and fluid injection apparatus positioned relative to the module to engage a filter element thereon, the filter clamping and fluid injection apparatus including a pair of first and second opposing engageable members to sealing engage a filter element on the module therebetween;

a fluid inlet tube connected to one of the opposing engageable members;

a fluid outlet tube connected to the other of the opposing engageable members;

a first motor to move the module relative to the filter clamping and fluid injection apparatus to register filter elements on the module to the filter clamping and fluid injection apparatus; and a second motor associated with the filter clamping and fluid injection apparatus to move the opposing engageable members into substantial sealing fluid communication relative to a filter element on the module.

7. The liquid test sample filtration apparatus of claim 6 wherein the second motor comprises a pneumatic cylinder.

8. The liquid test sample filtration apparatus of claim 6 wherein the module is configured and mounted for rotation.

9. The liquid test sample filtration apparatus of claim 6 wherein the module is configured and mounted for rotation, the module including a peripheral region, the peripheral region retaining the respective filter elements.

10. The liquid test sample filtration apparatus of claim 6 wherein the module is in the shape of a round carousel having a peripheral region, the respective filter elements being retained in the peripheral region.

11. The liquid test sample filtration apparatus of claim 6 wherein the module is in the shape of a round carousel having a peripheral region, a series of filter element retainers being provided about the carousel peripheral region to position and hold a series of filter elements on the carousel, the carousel peripheral region also including a recess cut-out area enabling the first and second opposing members to be engaged together without a filter element therebetween.

12. The liquid test sample filtration apparatus of claim 6 wherein the module is in the shape of a round carousel having a peripheral region, a series of slots being formed about the carousel peripheral region, one of the slots defining a cut-out in the carousel peripheral region enabling the first and second opposing members to be engaged together without a filter element therebetween, others of the slots defining retainers to position and hold a series of filter elements on the carousel.

13. The liquid test sample filtration apparatus of claim 6 wherein,
   the first member has a first recess configured to engage one end of a filter element, the first member including a first fluid passage communicating with the first recess to pass fluid between the first recess and externally of the first member; and
   the second member has a projection sized and shaped to matingly fit within the first member recess, the second member projection including a second recess configured to engage the other end of the filter element, the second member including a second fluid passage communicating with the second recess to pass fluid between the second recess and externally of the second member.

14. The liquid test sample filtration apparatus of claim 13 wherein the first member first recess and second member projection are conical in shape.

15. The liquid test sample filtration apparatus of claim 13 wherein the second member projection second recess is conical in shape.

16. The liquid test sample filtration apparatus of claim 13 wherein the first member first recess and second member projection are conical in shape, and the second member projection second recess is conical in shape.

17. The liquid test sample filtration apparatus of claim 6 wherein,
   the module is in the shape of a round carousel having a peripheral region, the respective filter elements being retained in the peripheral region;
   the first member has a first recess configured to engage one end of a filter element, the first member including a first fluid passage communicating with the first recess to pass fluid between the first recess and externally of the first member; and
   the second member has a projection sized and shaped to matingly fit within the first member recess, the second member projection including a second recess configured to engage the other end of the filter element, the second member including a second fluid passage communicating with the second recess to pass fluid between the second recess and externally of the second member.

18. The liquid test sample filtration apparatus of claim 17 wherein the round carousel comprises a series of filter element retainers provided about the carousel peripheral region to position and hold a series of filter elements on the carousel, the carousel peripheral region also including a recess cut-out area enabling the first and second opposing members to be engaged together without a filter element therebetween.

19. The liquid test sample filtration apparatus of claim 17 wherein the round carousel comprises a series of slots formed about the carousel peripheral region, one of the slots defining a cut-out in the carousel peripheral region enabling the first and second opposing members to be engaged together without a filter element therebetween, others of the slots defining retainers to position and hold a series of filter elements on the carousel.

20. The liquid test sample filtration apparatus of claim 6 wherein,
   the module is in the shape of a round carousel having a peripheral region, the respective filter elements being retained in the peripheral region;
   the first member has a first conical recess configured to engage one end of a filter element, the first member including a first fluid passage communicating with the first conical recess to pass fluid between the first recess and externally of the first member; and
   the second member has a conical projection sized and shaped to matingly fit within the first member conical recess, the second member conical projection including a second conical recess configured to engage the other end of the filter element, the second member including a second fluid passage communicating with the second conical recess to pass fluid between the second conical recess and externally of the second member.

21. The liquid test sample filtration apparatus of claim 20 wherein the round carousel comprises a series of filter element retainers provided about the carousel peripheral region to position and hold a series of filter elements on the carousel, the carousel peripheral region also including a recess cut-out area enabling the first and second opposing members to be engaged together without a filter element therebetween.

22. The liquid test sample filtration apparatus of claim 20 wherein the round carousel comprises a series of slots formed about the carousel peripheral region, one of the slots defining a cut-out in the carousel peripheral region enabling the first and second opposing members to be engaged together without a filter element therebetween, others of the slots defining retainers to position and hold a series of filter elements on the carousel.

23. An apparatus for engaging opposing ends of a filter element comprising:
   a first member having a first recess configured to engage one end of a filter element, the first member including a first fluid passage communicating with the first recess to pass fluid between the first recess and externally of the first member; and
   a second member positioned in opposing juxtaposition relative to the first member, the second member having a projection sized and shaped to matingly fit within the first member recess, the second member projection including a second recess configured to engage the other end of the filter element, the second member including a second fluid passage communicating with the second recess to pass fluid between the second recess and externally of the second member.

24. The apparatus for engaging opposing ends of a filter element of claim 23 wherein the first member first recess and second member projection are conical in shape.

25. The apparatus for engaging opposing ends of a filter element of claim 23 wherein the second member projection second recess is conical in shape.

26. The apparatus for engaging opposing ends of a filter element of claim 23 wherein the first member first recess and second member projection are conical in shape, and the second member projection second recess is conical in shape.

27. A rotatable module for use with a liquid test sample filtration apparatus, the filtration apparatus comprising a filter clamping and fluid injection apparatus for engaging filters on the rotatable module, the filter clamping and fluid injection apparatus comprising a pair of first and second opposing engageable members, the rotatable module comprising:

- a round carousel body having opposing faces and a peripheral edge;
- a series of filter element retainers provided about the carousel at the peripheral body edge, the filter element retainers being configured to retain a series of filter elements on the carousel for engagement by the filter clamping and fluid injection apparatus; and
- a cut-out slot provided in the carousel peripheral edge between two of the filter element retainers, the cut-out slot extending from one opposing face to the other and being sufficiently large to enable clamping engagement of the first and second opposing members therethrough.

28. The rotatable module for a liquid test sample filtration apparatus of claim 27 wherein the filter element retainers comprise a series of filter retaining slots formed in the peripheral edge.

29. The rotatable module for a liquid test sample filtration apparatus of claim 27 wherein the filter element retainers comprise a series of filter retaining slots formed in the peripheral edge, each retaining slot comprising a plurality of peripheral edge recesses.

* * * * *